（12）United States Patent
Tang et al.

(10) Patent No.: US 11,110,202 B1
(45) Date of Patent: Sep. 7, 2021

(54) CONSTRUCTION AND APPLICATION OF DIFFERENTIALLY REGULATED TISSUE-ENGINEERED NERVE GRAFTS

(71) Applicant: NANTONG UNIVERSITY, Jiangsu (CN)

(72) Inventors: Xin Tang, Jiangsu (CN); Cheng Sun, Jiangsu (CN); Gang Chen, Jiangsu (CN); Xiaosong Gu, Jiangsu (CN); Yumin Yang, Jiangsu (CN); Fei Ding, Jiangsu (CN); Yanpei Gong, Jiangsu (CN); Qianru He, Jiangsu (CN); Hongkui Wang, Jiangsu (CN); Mi Shen, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 17/044,837

(22) PCT Filed: Sep. 11, 2019

(86) PCT No.: PCT/CN2019/105280
§ 371 (c)(1),
(2) Date: Dec. 10, 2020

(87) PCT Pub. No.: WO2021/007941
PCT Pub. Date: Jan. 21, 2021

(30) Foreign Application Priority Data

Jul. 16, 2019 (CN) .......................... 201910640776.2

(51) Int. Cl.
*A61L 27/36* (2006.01)
*A61L 27/38* (2006.01)
(Continued)

(52) U.S. Cl.
CPC ......... *A61L 27/3675* (2013.01); *A61L 27/383* (2013.01); *A61L 27/54* (2013.01);
(Continued)

(58) Field of Classification Search
CPC .. A61F 2/00; A61F 2/0063; A61F 2250/0067; A61F 13/00063;
(Continued)

(56) References Cited

U.S. PATENT DOCUMENTS 6,676,675 B2 * 1/2004 Mallapragada ......... A61L 27/18
606/152
9,931,121 B2 * 4/2018 Agarwal ................ A61L 27/54
(Continued)

FOREIGN PATENT DOCUMENTS

| CN | 101664346 A | 3/2010 |
|---|---|---|
| CN | 102908207 A | 2/2013 |

(Continued)

OTHER PUBLICATIONS

Wang, Hongkui et al.; "Comparative transcriptomic profiling of peripheral efferent and afferent nerve fibres at different developmental stages in mice"; Scientific Reports; Aug. 10, 2018, vol. VIII, Article No. (2018) 8:11990.

*Primary Examiner* — George J Ulsh
(74) *Attorney, Agent, or Firm* — Novick, Kim & Lee, PLLC; Allen Xue (57) ABSTRACT

A differential tissue-engineered nerve including motor-like nerves and sensory-like nerves. The motor-like nerve and the sensory-like nerve respectively includes a motor-like nerve outer tube and a motor-like nerve fiber in the outer tube as well as a sensory-like nerve outer tube and a sensory-like nerve fiber in the outer tube. Schwann cells and/or fibroblasts derived from motor nerves and sensory nerves are respectively contained in surfaces or pores of the
(Continued)

motor-like and sensory-like nerve outer tubes. Transsynaptic signal molecules Neuroligin-1 and Neuroligin-2 are contained in surfaces or pores of the motor-like and sensory-like nerve fibers. Neuroligin-1 is selectively used to specifically promote synaptic remodeling of motor neurons, while Neuroligin-2 is selectively used to specifically promote synaptic remodeling of sensory neurons, so that repair efficiency of motor nerve cells and sensory nerve cells is improved.

9 Claims, 5 Drawing Sheets

(51) Int. Cl.
  *A61L 27/54* (2006.01)
  *A61L 27/56* (2006.01)
(52) U.S. Cl.
  CPC .......... *A61L 27/56* (2013.01); *A61L 2300/252* (2013.01); *A61L 2300/412* (2013.01); *A61L 2300/622* (2013.01); *A61L 2430/32* (2013.01)
(58) Field of Classification Search
  CPC ...... A61F 13/00068; A61F 2/82; A61F 2/945; A61F 2002/821; A61F 2002/91591; A61L 27/18; A61L 27/3675; A61L 27/383; A61L 27/54; A61L 2300/414; A61L 2300/64; A61L 2430/32; A61L 27/56; A61L 2300/622; A61L 2300/252; A61L 2300/412; A61B 17/1128; A61B 2017/1132; A61B 17/11; A61B 17/1114; A61B 2017/1107; A61B 2017/1135; A61B 2017/1139
  USPC ........................................................ 606/152
  See application file for complete search history.

(56) References Cited

U.S. PATENT DOCUMENTS

| | | | |
|---|---|---|---|
| 10,842,494 B2* | 11/2020 | Agarwal | A61F 2/00 |
| 2009/0024150 A1* | 1/2009 | Ahlers | A61B 17/1128 |
| | | | 606/152 |
| 2010/0168625 A1* | 7/2010 | Swain | A61M 1/90 |
| | | | 601/6 |
| 2011/0125170 A1* | 5/2011 | Hoke | A61L 27/3878 |
| | | | 606/152 |
| 2013/0234372 A1* | 9/2013 | Almutairi | A61L 27/18 |
| | | | 264/496 |
| 2018/0291123 A1* | 10/2018 | Smith Callahan | A61L 27/20 |
| 2020/0155156 A1* | 5/2020 | Ducic | A61B 17/1128 |

FOREIGN PATENT DOCUMENTS

| | | |
|---|---|---|
| CN | 104623738 A | 5/2015 |
| CN | 207722144 U | 8/2018 |
| WO | 2013066619 A1 | 5/2013 |
| WO | 20190135812 A2 | 7/2019 |

* cited by examiner

CONSTRUCTION AND APPLICATION OF DIFFERENTIALLY REGULATED TISSUE-ENGINEERED NERVE GRAFTS

BACKGROUND

Technical Field

The present invention belongs to the field of biomedicine, and particularly relates to a differential tissue-engineered nerve, which can differentially regulate repair of motor nerves and sensory nerves.

Related Art

Peripheral nerve injury is a common clinical disease. With social and economic development and aging of a population structure, acute trauma and chronic degenerative diseases resulting from accidents lead to a significant increase trend in peripheral neuropathy. The peripheral nerve injury leads to impaired motor and sensory functions in a corresponding part of a patient. Recovery of the functions after injury depends mainly on precise, selective, and guided growth of regenerative axons for specific motor and sensory pathways. Clinically, nerve repair is mainly performed by direct suture without tension at broken ends, autologous or allogeneic nerve transplantation, tissue-engineered nerve grafts and the like. Because the direct suture of the broken ends is only suitable for less severe local trauma, and many inconveniences and disadvantages are present in actual operation of autologous or allogeneic nerve transplantation, a currently main research direction of peripheral nerve repair is to explore construction of a suitable tissue-engineered nerve.

Under normal physiological state, motor and sensory nerve fibers of a peripheral nervous system grow orderly in certain directions in corresponding perineuria. After nerve injury, if a catheter only made of material is bridged at a local part of the injury, regeneration modes of motor and sensory nerve fibers are disordered and chaotic, and a misconnection rate of the nerve fibers exists. In addition, even if the nerve fibers eventually find the target organ to be innervated at a later stage, a rate of nerve regeneration has been severely affected. More seriously, an effector organ at a distal portion of nerve fiber ending cannot fully recover its function due to long-term denervation, for example, a process of atrophy of target muscle is irreversible. Therefore, proper intervention is carried out in an early stage of regeneration to promote accurate and orderly growth of the motor and sensory nerve fibers, so that a rate and efficiency of peripheral nerve regeneration can be improved.

Chinese patent document CN102908207A discloses a tissue-engineered nerve graft prepared based on a bioprinting technique, which includes an outer tube and a nanofiber scaffold in the tube, wherein a diameter of the outer tube is 1-9 mm. A wall thickness is 0.5-1 mm. A diameter of the nanofiber scaffold in the tube is 0.1 mm. The number of the scaffolds is 5-30. The scaffolds are uniformly distributed in the tube. Nutritional factors and/or cells are coated inside or on a surface of the scaffold and inner and outer surfaces of the outer tube. Chinese patent document CN104623738A discloses a tissue-engineered nerve graft with a suspension fiber scaffold, which includes a catheter and a fiber scaffold in the catheter, wherein a plurality of suspension fibers are arranged in a length direction of fibers on each fiber scaffold and connected with an inner wall of the catheter, and the fiber scaffold is suspended in the catheter through the suspension fibers. These studies utilize the bioprinting technique, use nanofibers as "bridges" for nerve cell growth and ensure that nerve cells can grow directionally along the fiber scaffold. However, during the actual peripheral nerve repair, a motor nerve and a sensory nerve cannot be well distinguished, and the problem of nerve fiber misconnection still exists.

SUMMARY

According to a unique anatomical structure of peripheral nerves, the present invention designs and constructs a differential tissue-engineered nerve, which can differentially regulate repair of motor nerves and sensory nerves.

Specific technical schemes of the present invention are as follows:

a differential tissue-engineered nerve, including motor-like nerves and sensory-like nerves, the motor-like nerve includes a motor-like nerve outer tube and a motor-like nerve fiber in the outer tube, Schwann cells and/or fibroblasts derived from motor nerves are contained in surface or pores of the motor-like nerve outer tube and a transsynaptic signal molecule Neuroligin-1 is contained in surface or pores of the motor-like nerve fiber; and the sensory-like nerve includes a sensory-like nerve outer tube and a sensory-like nerve fiber in the outer tube, Schwann cells and/or fibroblasts derived from sensory nerves are contained in surface or pores of the sensory-like nerve outer tube and a transsynaptic signal molecule Neuroligin-2 is contained in surface or pores of the sensory-like nerve fiber.

Findings of the present invention indicate that Neuroligin-1 can specifically promote synaptic remodeling of motor neurons, and Neuroligin-2 can specifically promote synaptic remodeling of sensory neurons. Through applying the two to motor and sensory nerve regeneration respectively, very good nerve repair effects can be achieved.

Preferably, a ratio of the number of the Schwann cells and/or fibroblasts derived from the motor nerves to the number of the Schwann cells and/or fibroblasts derived from the sensory nerves is 1:(1 to 5). In order to ensure that a regeneration rate of nerve cells on the motor-like nerve fibers is consistent with that of nerve cells on the sensory-like nerve fibers in the present invention, the ratio of the number of the Schwann cells and/or fibroblasts derived from the motor nerves to the number of the Schwann cells and/or fibroblasts derived from the sensory nerves is more preferably 1:3.

In a preferred scheme, a mass ratio of Neuroligin-1 to Neuroligin-2 is 1:1.

Preferably, a transsynaptic signal molecule Neurexin-1β is further contained on the motor-like nerve fibers and/or sensory-like nerve fibers according to the present invention. A mass ratio of Neurogligin-1 to Neurexin-1β on the motor-like nerve fibers is preferably 1:(0.01-10), more preferably 1:5. A mass ratio of Neuroligin-2 to Neurexin-1β on the sensory-like nerve fibers is 1:(0.01-10), more preferably 1:5.

The differential tissue-engineered nerve according to the present invention may be prepared by techniques disclosed in the prior art, such as casting, freeze-drying molding, an electrospinning technique, a three-dimensional bioprinting technique, preferably the three-dimensional bioprinting technique.

The present invention may print Schwann cells and/or fibroblasts derived from the motor and sensory nerves, and the transsynaptic signal molecules Neuroligin-1, Neuroligin-2, Neurexin-1β (or microspheres prepared and containing the transsynaptic signal molecules) with the motor nerve fibers and sensory nerve fiber materials as raw materials by using the bioprinting technique, and Schwann cells and/or fibroblasts derived from the motor and sensory nerves, and the transsynaptic signal molecules Neuroligin-1, Neuroligin-2, and Neurexin-1β (or microspheres prepared and containing the transsynaptic signal molecules) may also be printed, coated or passively adsorbed at corresponding locations on the nerve fibers, respectively.

In a preferred scheme according to the present invention, the transsynaptic signal molecules Neuroligin-1, Neuroligin-2 and Neurexin-1β may be embedded in microspheres (preferably sustained-release microspheres) to improve stability and ensure biological activity and adhesion in tissue-engineered nerves.

In a preferred scheme, PLGA microspheres are used, and a preparation method is as follows:

Polylactic acid-glycolic acid copolymer (PLGA, a molar ratio of lactic acid to ethanol is 53:47, and molecular weight [MW] is 25 kDa). The PLGA microspheres are prepared by a water/oil/water multiple emulsion method. 100 mg of PLGA is dissolved in 1 mL of dichloromethane, then emulsified into 3 mL of a 7% (w/v) poly(vinyl alcohol) (PVA) aqueous solution, and ultrasonicated for 1 min to prepare an emulsion of a first step. Then, the above solution is added to 50 mL of a 1% (w/v) poly(vinyl alcohol) (PVA) aqueous solution (containing 2% isopropanol), and ultrasonicated again for 3 min to form an emulsion of a second step. The emulsion of the second step as mentioned above is slowly stirred overnight at room temperature, and the residual dichloromethane is fully volatilized. The PLGA microspheres are obtained by centrifugation sedimentation at 13,000 rpm at 4° C. for 5 min. The PLGA microspheres are washed twice with ddH$_2$O and resuspended in 0.4 mL of ddH$_2$O for standby application.

The motor-like nerves and the sensory-like nerves according to the present invention are of nerve conduit structures including outer tubes and motor-like nerve fibers and sensory-like nerve fibers in the tubes, preferably having an outer tube diameter of 1-9 mm and a wall thickness of 0.5-1 mm, and the motor-like nerve fibers and the sensory-like nerve fibers have a diameter of 0.01-0.1 mm and a number of 5-30.

The differential tissue-engineered nerve according to the present invention is made of a degradable polymer material selected from one or more of polylactic acid, polyglycolic acid, collagen, gelatin, chitosan, silk fibroin.

In a preferred scheme of the present invention, the motor-like nerves and the sensory-like nerves are arranged in a multi-branched manner in one or more of a parallel type, a Y type, a dendritic type, and a tooth comb type. Relative separation of the motor nerves and the sensory nerves in space can be ensured in a better fashion and accuracy of bridging is improved. Relative positions of the motor-like nerves and the sensory-like nerves may be further designed and arranged by using an outer cannula, a suspension fiber, a scaffold and the like so as to have a fixed shape.

The present invention is also directed to provide application of the tissue-engineered nerve according to the present invention in the repair of peripheral nerve defects.

Advantages according to the present invention:

The present invention discovers different effects of different Neuroligins on motor nerve cells and sensory nerve cells for the first time, selectively uses Neuroligin-1 to specifically promote synaptic remodeling of motor neurons, and uses Neuroligin-2 to specifically promote synaptic remodeling of sensory neurons, so that repair efficiency of the motor nerve cells and the sensory nerve cells is improved.

The present invention further explores that the repair rate of Neuroligin-1 and Neuroligin-2 for promoting the motor nerve cells and the sensory nerve cells, so that the regeneration rate of the motor nerve is consistent with that of the sensory nerve in the tissue-engineered nerve according to the present invention, and the regeneration rate of the peripheral nerves is improved.

With a research method of tissue engineering, the present invention constructs a tissue-engineered nerve biomimicking anatomical structure/local microenvironment in a dual way by locally simulating and slowly releasing synapse-associated protein suitable for specific growth of axon of motor and sensory neuron in peripheral nerve injury, and combining a 3D motor and sensory microenvironment consisting of Schwann cells and fibroblasts, thereby being beneficial to improving rate and efficiency of peripheral nerve regeneration.

BRIEF DESCRIPTION OF THE DRAWINGS

FIG. 1A is an immunocytochemical staining showing distribution and expression of Synaptophysin and PSD-95 as synapse-associated protein for Neuroligin-1 and Neuroligin-2 respectively acting on motor neurons and sensory neurons. FIG. 1B is a histogram of synaptic areas of the presynaptic membrane protein Synaptophysin and the postsynaptic membrane PSD-95 as a percentage of a total neurites area for Neuroligin-1 and Neuroligin-2 respectively acting on motor neurons and sensory neurons (**vs.Neuroligin-1 in sensory neuron; ##vs.Neuroligin-2 in motor neuron, $P<0.01$).

FIG. 2A is an immunocytochemical staining showing distribution and expression of Synaptophysin and PSD-95 as synapse-associated protein for Neurexin-1β and Neurexin-1β in combination with Neuroligin-1 or Neuroligin-2 respectively acting on motor neurons and sensory neurons. FIG. 2B is a histogram of synaptic areas of the presynaptic membrane protein Synaptophysin and the postsynaptic membrane PSD-95 as a percentage of a total neurites area for Neurexin-1β and Neurexin-1β in combination with Neuroligin-1 or Neuroligin-2 respectively acting on motor neurons and sensory neurons (**vs.Neuroligin-1 200 ng/mL+Neurexin-1β 1 μg/mL in motor neuron; ##vs.Neuroligin-2 200 ng/mL+Neurexin-1β1 μg/mL in sensory neuron, $P<0.01$).

FIG. 4A is a representative diagram of CMAP in each experimental group. FIG. 4B shows statistical results of the CMAP of each experimental group as a percentage of Autograft. (n=6, *vs.optimized TENG, $P<0.05$; **vs.optimized TENG, $P<0.01$).

FIG. 5A shows results of a mechanical pain test in each experimental group (n=6, *vs.optimized TENG, P<0.05). FIG. 5B shows results of a heat-sensitive pain test of each experimental group (n=6, *vs.optimized TENG, P<0.05; **vs.optimized TENG, P<0.01).

DETAILED DESCRIPTION

Specific steps of the present invention are illustrated by the following embodiments, but are not limited by such embodiments.

Terms used in the present invention generally have meanings as commonly understood by those of ordinary skill in the art, unless otherwise indicated.

The present invention is described in further detail below with reference to specific embodiments and with reference to data. It should be appreciated that the embodiments are merely illustrative of the present invention and are not intended to limit the scope of the present invention.

In the following embodiments, various processes and methods not described in detail are conventional methods well known in the art.

The present invention is further described below with reference to specific embodiments.

Embodiment 1 Promoting Effects of Neuroligin-1 and Neuroligin-2 on Synapses in Motor and Sensory Neurons (1) Culture of motor neurons: a SD rat pregnant for 15 d-16 d was dissected under an anatomical lens to remove ventral tunica, dorsal root ganglia and blood vessels of a spinal cord, and a ventral spinal cord of a fetal rat was carefully separated and placed in a petri dish containing ice-cold anatomical fluid. A tissue piece having a size of 0.5 cm$^3$ was cut by a microscissor and then transferred to a 15 mL centrifuge tube. After adding 0.25% trypsin and 200 U/ml DNase, digestion was performed at 37° C. for 30 min, and then digestion was terminated by adding DMEM+10% FBS. Centrifugation was performed at 1000 r/min for 5 min, and supernatant was discarded. 5 mL of Optiprep separation solution was added, and density gradient centrifugation was performed at 3000 r/min for 15 min. Then liquid in the centrifuge tube was divided into 3 layers, wherein the middle layer contained spinal motor neurons. The middle layer was carefully pipetted to a 15 mL centrifuge tube. 3 mL of medium was added. Centrifugation was performed at 1000 r/min for 5 min, and supernatant was discarded to remove cell debris. Cells were resuspended by adding DMEM+10% FBS, and cell suspension was added to an uncoated 6-well plate. Differential attachment was performed for 1 h. Unattached cells were collected and centrifuged, and a Neurobasal complete medium (97% Neurobasal+2% B27+1% GluMAX) was added to resuspend the cells. Cell suspension was seeded at 1×10$^5$/mL into a 24-well plate pre-coated with polylysine. The medium was replaced once at 12 h and then half of the medium was replaced every 3 d.

(2) Culture of sensory neurons: a SD rat pregnant for 17 d-18 d was dissected to take out a fetal rat. The fetal rat was placed on ice. A spinal canal was opened under an anatomical lens to remove a spinal cord. L4-6 dorsal root ganglia were carefully taken out, and outer membranes of the dorsal root ganglia were removed as much as possible to trim nerve roots. The dorsal root ganglia were transferred into 0.25% trypsin and 0.5 g/L collagenase and digested at 37° C. for 30 min. Digestion was terminated by the addition of DMEM+ 10% FBS. Centrifugation was performed at 1000 r/min for 5 min, and supernatant was discarded. Cells were resuspended by adding a Neurobasal complete medium (97% Neurobasal+2% B27+1% GluMAX). Cell suspension was seeded at 1×10$^5$/mL into a 24-well plate pre-coated with polylysine. On the third day of culture, 20 mg/L of 5-fluorouracil was added to inhibit proliferation-type non-neuronal cells, and after 48 hours, the medium was replaced with a Neurobasal complete medium, and then half of the medium was replaced every 3 d.

After motor neurons and sensory neurons were cultured for 10 d in vitro respectively, each of them was divided into two groups. Neuroligin-1 (final concentration of 200 ng/mL) and Neuroligin-2 (final concentration of 200 ng/mL) were respectively added and culture is continued for 24 h. A mixture was washed twice with 0.01 M PBS (pH of 7.2), fixed with 4% paraformaldehyde at room temperature for 10 min, blocked with a blocking solution at room temperature for 1 h, and added with primary antibodies mouse anti-Synaptophysin polyclonal antibody (concentration 1:600) and rabbit anti-PSD-95 polyclonal antibody (concentration of 1:800) and placed at 4° C. overnight (a negative control without primary antibody was set in an experiment). Washing was performed three times with 0.01 M PBS (pH 7.2). TRITC donkey anti rabbit IgG (concentration of 1:200) and FITC donkey-anti-mouse IgG (concentration of 1:200) were added and incubated at room temperature for 2 h. Washing was performed twice with 0.01 M PBS (pH of 7.2). A nucleus was stained with Hoechst (5 μg/ml). A section was sealed with a fluorescent sealing liquid and observed under a laser confocal microscope (LEICA-SP2, Germany).

Figure 1:
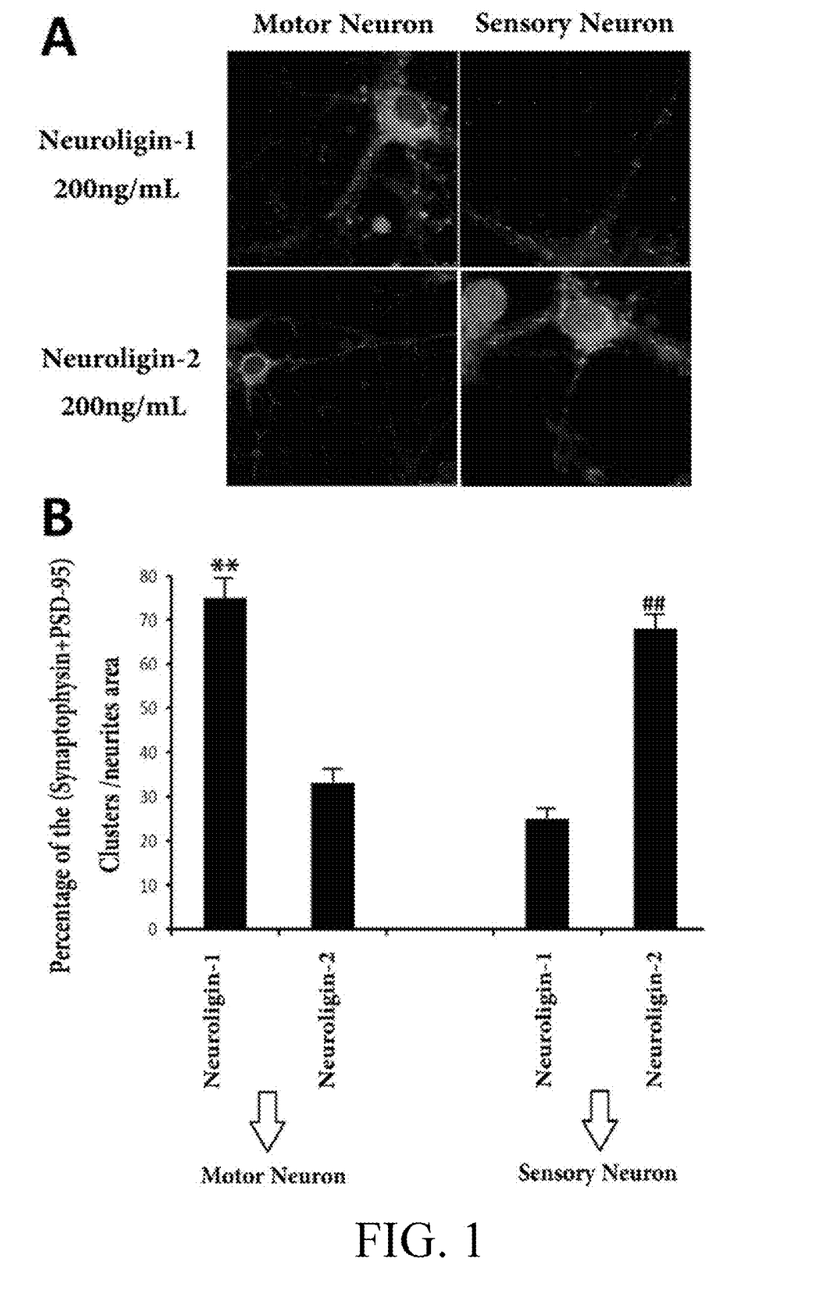
FIG. 1 is an immunocytochemical staining showing effects of Neuroligin-1 and Neuroligin-2 respectively acting on motor neurons and sensory neurons on synapse formation.

Results of immunocytochemical staining are shown in FIG. 1. FIG. 1A is an immunocytochemical staining showing distribution and expression of Synaptophysin and PSD-95 as synapse-associated protein for Neuroligin-1 (final concentration of 200 ng/mL) and Neuroligin-2 (final concentration of 200 ng/mL) respectively acting on motor neurons and sensory neurons. FIG. 1B is a histogram of synaptic areas of the presynaptic membrane protein Synaptophysin and the postsynaptic membrane PSD-95 as a percentage of a total neurites area for Neuroligin-1 and Neuroligin-2 respectively acting on motor neurons and sensory neurons. The results show that the presynaptic membrane protein Synaptophysin (green) and the postsynaptic membrane PSD-95 (red) had a synaptic area of 75% or above of the total neurites area after Neuroligin-1 acted on the motor neurons, while the presynaptic membrane protein Synaptophysin (green) and the postsynaptic membrane PSD-95 (red) had a synaptic area of 33% of the total neurites area after Neuroligin-1 acted on the sensory neurons, indicating that Neuroligin-1 only specifically promotes synapse formation in the motor neurons.

The presynaptic membrane protein Synaptophysin (green) and the postsynaptic membrane PSD-95 (red) had a synaptic area of 68% or above of the total neurites area after Neuroligin-2 acted on the sensory neurons, while the presynaptic membrane protein Synaptophysin (green) and the postsynaptic membrane PSD-95 (red) had a synaptic area of 25% of the total neurites area after Neuroligin-2 acted on the motor neurons, indicating that Neuroligin-2 only specifically promotes synapse formation in the sensory neurons.

Embodiment 2 Promoting Effect of Neurexin-1β in Combination with Neuroligin-1 or Neuroligin-2 on Synapse Formation Motor neurons and sensory neurons were cultured for 10 d in vitro and then divided into groups as follows. Neurexin-1β in combination with Neuroligin-1 or Neuroligin-2 was added to motor neuron and sensory neuron media, respectively:

Motor Neuron Group:

(1) Neurexin-1β (final concentration of 200 ng/mL)+Neuroligin-1 (final concentration of 200 ng/mL);

(2) Neurexin-1β (final concentration of 1 μg/mL)+Neuroligin-1 (final concentration of 200 ng/mL);

(3) Neurexin-1β (final concentration of 1 μg/mL).

Sensory Neuron Group:

(4) Neurexin-1β (final concentration of 200 ng/mL)+Neuroligin-2 (final concentration of 200 ng/mL);

(5) Neurexin-1β (final concentration of 1 μg/mL)+Neuroligin-2 (final concentration of 200 ng/mL);

(6) Neurexin-1β (final concentration of 1 μg/mL).

Figure 2:
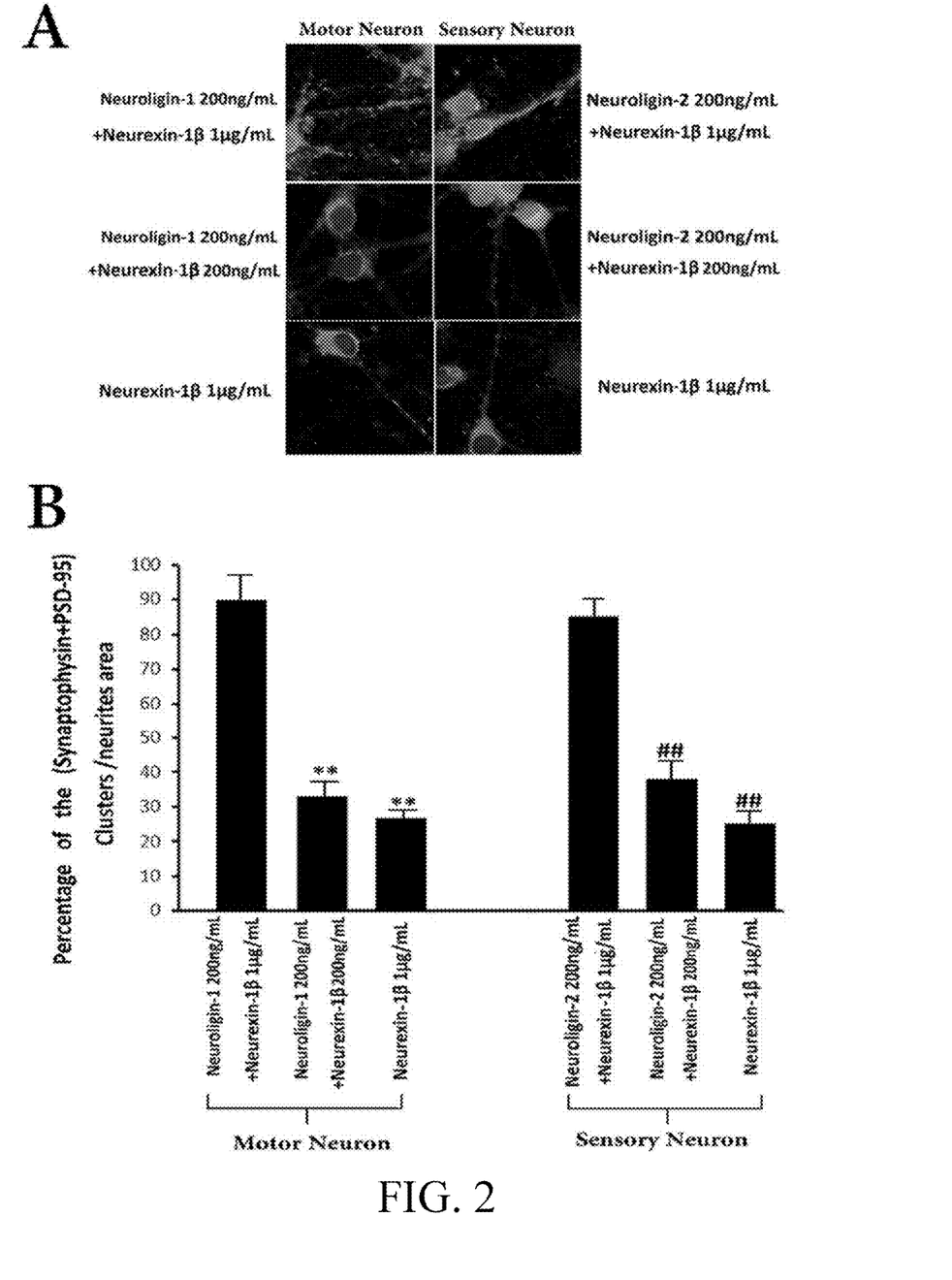
FIG. 2 is an immunocytochemical staining showing a dose-related synergistic effect between Neurexin-1β and Neuroligins.

The culture was continued for 24 h. Results of immunocytochemical staining are shown in FIG. 2. FIG. 2A is an immunocytochemical staining showing distribution and expression of Synaptophysin and PSD-95 as synapse-associated protein for different concentrations of Neurexin-1β (final concentration of 1 μg/mL) alone or Neurexin-1β (final concentration of 1 μg/mL or 200 ng/mL) in combination with Neuroligin-1 (final concentration of 200 ng/mL) or Neuroligin-2 (final concentration of 200 ng/mL) respectively acting on motor neurons and sensory neurons. FIG. 2B is a histogram of synaptic areas of the presynaptic membrane protein Synaptophysin and the postsynaptic membrane PSD-95 as a percentage of a total neurites area for different concentrations of Neurexin-1β alone or Neurexin-1β in combination with Neuroligin-1 or Neuroligin-2 respectively acting on motor neurons and sensory neurons. The results show that the presynaptic membrane protein Synaptophysin (green) and the postsynaptic membrane PSD-95 (red) had a synaptic area of 33% of the total neurites area for the motor neurons when a mass ratio of Neuroligin-1 to Neurexin-1β was 1:1. The presynaptic membrane protein Synaptophysin (green) and the postsynaptic membrane PSD-95 (red) had a synaptic area of 90% of the total neurites area for the motor neurons when the mass ratio of Neuroligin-1 to Neurexin-1β was 1:5. The presynaptic membrane protein Synaptophysin (green) and the postsynaptic membrane PSD-95 (red) had a synaptic area of 26% of the total neurites area for the motor neurons when the final concentration of Neurexin-1β was 1 μg/mL.

The presynaptic membrane protein Synaptophysin (green) and the postsynaptic membrane PSD-95 (red) had a synaptic area of 38% of the total neurites area for the sensory neurons when a mass ratio of Neuroligin-2 to Neurexin-1β was 1:1. The presynaptic membrane protein Synaptophysin (green) and the postsynaptic membrane PSD-95 (red) had a synaptic area of 85% of the total neurites area for the sensory neurons when the mass ratio of Neuroligin-2 to Neurexin-1β was 1:5. The presynaptic membrane protein Synaptophysin (green) and the postsynaptic membrane PSD-95 (red) had a synaptic area of 23% of the total neurites area for the sensory neurons when the final concentration of Neurexin-1β was 1 μg/mL.

The results indicate that Neurexin-1β in combination with Neuroligin-1 or Neuroligin-2 can promote synapse formation, and especially when the mass ratio of Neuroligin-1/Neuroligin-2 to Neurexin-1β is 1:5, the synergistic effect of promoting synaptic formation is optimally exerted.

Embodiment 3 Construction of a Differential Tissue-Engineered Nerve According to the Present Invention 1. Preparation of Sustained-Release Microspheres Containing Neuroligin-1, Neuroligin-2 and Neurexin-1β Recombinant Protein Polylactic acid-glycolic acid copolymer (PLGA, a molar ratio of lactic acid to ethanol was 53:47, and molecular weight [MW] was 25 kDa). PLGA microspheres were prepared by a water/oil/water multiple emulsion method. 100 mg of PLGA was dissolved in 1 mL of dichloromethane, and then emulsified into 3 mL of a 7% (w/v) poly(vinyl alcohol) (PVA) aqueous solution, and ultrasonicated for 1 min to prepare an emulsion of a first step. Then, the above solution was added to 50 mL of a 1% (w/v) poly(vinyl alcohol) (PVA) aqueous solution (containing 2% isopropanol), and ultrasonicated again for 3 min to form an emulsion of a second step. The emulsion of the second step as mentioned above was slowly stirred overnight at room temperature, and the residual dichloromethane was fully volatilized. The PLGA microspheres were obtained by centrifugation sedimentation at 13,000 rpm at 4° C. for 5 min. The PLGA microspheres were washed twice with ddH$_2$O and resuspended in 0.4 mL of ddH$_2$O for standby application.

A prepared 0.4 mL PLGA microsphere aqueous solution (10 mg/mL) and polyetherimide (PEI, ¼ molecular weight [MW] was 25 kDa) were co-dissolved in ddH$_2$O, and an obtained solution was added to the PLGA microsphere solution at different nitrogen/phosphorus ratios and vortexed slightly. A PEI-modified PLGA microsphere aqueous solution was prepared and incubated for 20 min at room temperature. Microspheres were obtained by centrifugation sedimentation at 13,000 rpm at 4° C. for 5 min, washed twice with ddH$_2$O, and resuspended by adding 0.4 mL of ddH$_2$O. 1 mL of PEI-modified PLGA microsphere aqueous solution (10 mg/mL) was mixed with 10 μL of 200 ng/mL-1 μg/mL Neuroligin-1 (Recombinant Rat NLGN1Protein, Creative Biomart, Catalog #NLGN1-3995R), 200 ng/mL-1 μg/mL Neuroligin-2 (Recombinant Rat NLGN2Protein, Creative Biomart, Catalog #NLGN2-3996R) and 200 ng/mL-5 μg/mL Neurexin-1β (Recombinant Rat Neurexin-1-beta, Cusabio, Catalog #Q63373) recombinant protein solutions, respectively, and incubated for 90 min at room temperature to form PEI-modified sustained-release microspheres with Neuroligin-1, Neuroligin-2 and Neurexin-1β recombinant protein, respectively.

2. Rat Schwann cells and/or fibroblasts derived from motor nerves and Schwann cells and/or fibroblasts derived from sensory nerves were prepared with reference to Comparative transcriptomic profiling of peripheral efferent and afferent nerve fibres at different developmental stages in mice (Scientific Reports, 2018, 10; 8(1): 11990.doi: 10.1038), Differential Gene Expression in Primary Cultured Sensory and Motor Nerve Fibroblasts (Frontiers in Neuroscience, 2019, Jan. 9; 12:1016.doi: 10.3389), and Comparison in the biological characteristics between primary cultured sensory and motor Schwann cells" (Neuroscie Lett., 2012, 521(1):57-61).

3. Construction of a Differential Tissue-Engineered Nerve by 3D Bioprinting 3.1 Preparation of Silk Fibroin Fibers Containing Sustained-Release Microspheres Bombyx mori silk was routinely boiled twice with a 0.05M Na$_2$CO$_3$ aqueous solution for 30 min each time to fully remove sericin from the silk, washed thoroughly with deionized water, and air-dried at room temperature to obtain silk fibroin fibers SF. The silk fibroin fibers had a diameter of 10-30 μm and were sterilized under high temperature and high pressure for standby application.

Sustained-release microspheres containing Neuroligin-1, Neuroligin-2 and Neurexin-1β recombinant protein were immobilized on the silk fibroin fibers by using natural, non-toxic, and compatible genipin as a biological cross-linker to obtain silk fibroin fibers containing the Neuroligin-1, Neuroligin-2 and Neurexin-1β recombinant protein sustained-release microspheres. (The microspheres with the same content of transsynaptic signal molecules can be prepared, and a ratio of Neuroligin-1, Neuroligin-2 and Neurexin-1β on nerve fibers can be controlled by adjusting the use amount of the sustained-release microspheres. PEI-modified PLGA sustained-release microspheres were immobilized on the silk fibroin fibers by the crosslinker genipin interacting with silk fibroin and a side chain amino group of PLGA respectively through a bifunctional group.

3.2 Functional biological ink for 3D printing was prepared by taking silk fibroin/gelatin solution as a carrier and compounding the Schwann cells and/or fibroblasts derived from the motor nerves and the Schwann cells and/or fibroblasts derived from the sensory nerves. A tissue-engineered nerve graft biomimicking structure/microenvironment in a dual way was printed out by outputting a digital printing instruction of a rat sciatic nerve scaffold to an ink-jet 3D bioprinter and using the functional biological ink.

(1) A silk fibroin solution was prepared. Silk was magnetically stirred in a water bath at 80° C. until completely dissolved in a ternary solution of a molar ratio of $CaCl_2$: $H_2O$:$C_2H_5OH$=1:8:2. A silk fibroin solution was dissolved in a LiBr aqueous solution at 40° C. for 2 h, placed in a dialysis bag and continuously dialyzed with deionized water for 3 d until conductivity of the deionized water outside the dialysis bag was basically unchanged, and then the silk fibroin solution with a mass fraction of 4% was obtained.

(2) A gelatin solution was prepared. 15 g of gelatin material was weighed, slowly added into 100 g of $H_2O$ while stirring, fully swelled, then heated to about 80° C. to accelerate dissolution, and was kept warm for 3 h to obtain a homogeneous polymer solution, which was sterilized under high pressure steam for standby application.

(3) A mixed solution of a silk fibroin/gelatin solution and a cell culture solution was prepared. The Schwann cells and fibroblasts cultured to the third generation were digested with 0.25% trypsin, then collected in a 15 mL centrifuge tube, and centrifuged at 1000 r/min for 5 min, and supernatant was discarded. The cell culture solution with a cell concentration of $5×10^5$-$5×10^6$ cells/mL was transferred to the silk fibroin/gelatin solution at a volume ratio of 1:100, and cells derived from the motor nerves were uniformly stirred to form a first mixed solution A, and cells derived from the sensory nerves were uniformly stirred to form a second mixed solution B.

(4) The first mixed solution A and the second mixed solution B were respectively loaded into two sets of different syringes of the printer, and a running program of the printer was set. A stable flow rate of the functional biological ink was controlled to be 180 μl/min by a micro-pump, and a nozzle needle of the printer had a diameter of 200 so that the cells can pass freely without clogging. Pulse frequency of a supercharger was 15 v, which had no effect on cell viability. A moving speed of a printer nozzle in an XY axis direction was 1-50 mm/s. Moving height of the printer nozzle in a Z axis direction was 100-500 μm. A time interval between finish of printing of the printer nozzle in the XY axis direction and start of printing of the printer nozzle in the Z axis direction was controlled within 2 min.

(5) A mixed solution of cells and the silk fibroin/gelatin solution was printed layer by layer on a surface of a petri dish. Ambient temperature was 20° C., and relative humidity was 65%. Time for cross-linking and sizing was 5-10 min. A pipe diameter was 1-9 mm, and a wall thickness was 0.5-1 mm.

Figure 3:
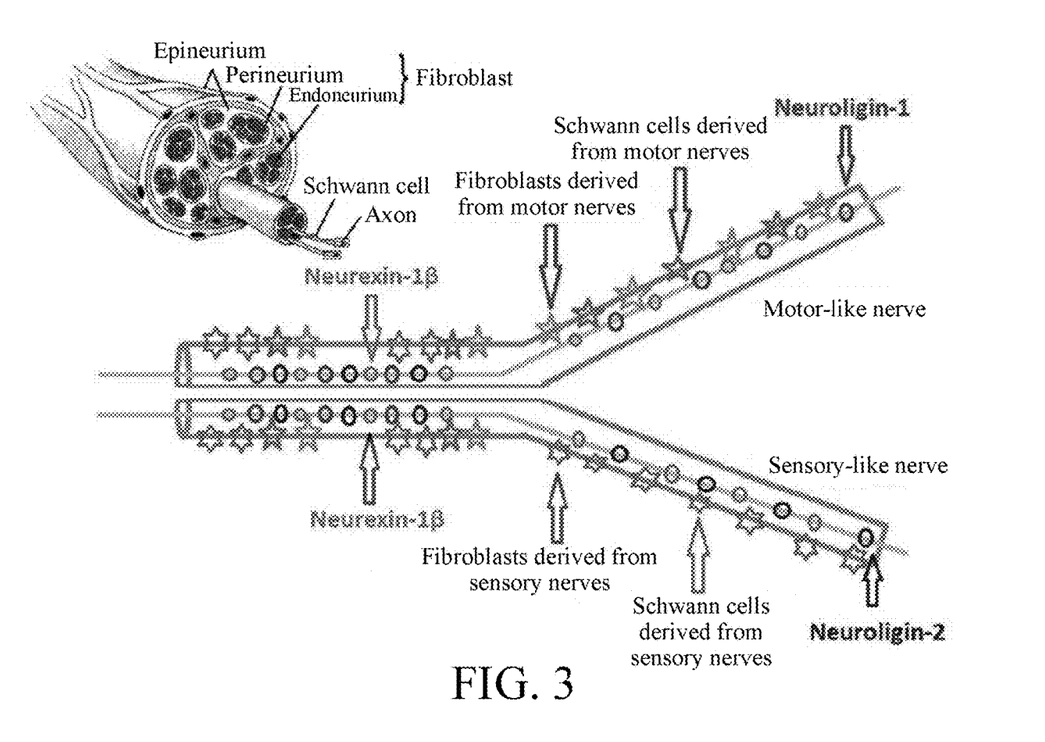
FIG. 3 is a schematic diagram of a differential tissue-engineered nerve according to the present invention.

(6) Silk fibroin suspension fibers containing the Neuroligin-1 and Neurexin-1β recombinant protein sustained-release microspheres were immobilized in a 3D-printed motor-like nerve outer tube, and silk fibroin suspension fibers containing the Neuroligin-2 and Neurexin-1β recombinant protein sustained-release microspheres were immobilized in a 3D-printed sensory-like nerve outer tube to form a Y-shaped catheter, which is as shown in FIG. 3, and a differential tissue-engineered nerve was obtained by combination and construction.

Embodiment 4 Application of a differential tissue-engineered nerve according to the present invention in repair of nerve defects 1. Preparation of a Model of Sciatic Nerve Defects.

SPF male SD rats were randomly divided into 5 groups (n=6):

(1) a mixed motor and sensory group (Mixed): motor-like and sensory-like nerve fibers were mixed into a nerve conduit with a traditional cylindrical biomaterial as a scaffold, and motor-like and sensory-like nerves were not specifically distinguished. A ratio of the number of Schwann cells and/or fibroblasts on motor-like and sensory-like nerves was 1:3. A mass ratio of Neuroligin-1 to Neurexin-1β on the motor-like nerve fibers was 1:5. A mass ratio of Neuroligin-2 to Neurexin-1β on the sensory-like nerve fibers was 1:5. The number of cells and the ratio of factors were the same as those of an optimized motor-specific and sensory-specific tissue-engineered nerve group (optimized TENG), except that the motor-like and sensory-like nerves were not specifically distinguished and mixed in a conventional conduit.

(2) a motor-specific and sensory-specific tissue-engineered nerve group (TENG): the motor-like and sensory-like nerves were distinguished by the Y-shaped scaffold obtained by the method of Embodiment 3, and the ratio of the number of the Schwann cells and/or fibroblasts on the motor-like and sensory-like nerves was 1:1. The mass ratio of Neuroligin-1 to Neurexin-1β on the motor-like nerve fibers was 1:5. The mass ratio of Neuroligin-2 to Neurexin-1β on the sensory-like nerve fibers was 1:5.

(3) an optimized motor-specific and sensory-specific tissue-engineered nerve group (optimized TENG): the motor-like and sensory-like nerves were distinguished by the Y-shaped scaffold obtained by the method of Embodiment 3, and the ratio of the number of the Schwann cells and/or fibroblasts on the motor-like and sensory-like nerves was 1:3. The mass ratio of Neuroligin-1 to Neurexin-1β on the motor-like nerve fibers was 1:5. The mass ratio of Neuroligin-2 to Neurexin-1β on the sensory-like nerve fibers was 1:5.

(4) a material only group (Scaffold), which was a negative control group, that is, an extraneural catheter was constructed using only silk fibroin/gelatin as a scaffold material and no corresponding supporting cells were mixed in the material, and the inside thereof was hollow and had no sustained-release microspheres or cytokines.

(5) an autologous nerve group (Autograft), which was a positive control group, that is, a removed 10 mm sciatic nerve was inverted in-situ in a horizontal direction of a long axis and then sutured at a broken end.

A 10 mm defect model of a rat sciatic nerve was prepared by routine surgery.

2. Evaluation of Recovery of Postoperative Motor Function

Electrophysiological Function Test of Compound Muscle Action Potentials (CMAPs)

Rats were electrophysiologically tested at room temperature 12 weeks after surgery. The rats were weighed and intraperitoneally injected with a compound anesthetic (0.2-

0.3 mL per 100 g of rat body weight). After successful anesthesia, sciatic nerves were exposed, and the sciatic nerves were carefully separated by a glass dividing needle. Recording electrodes were penetrated into gastrocnemius muscle bellies. Interference electrodes were placed in a surface of knee skin of the rats. Stimulating electrodes were placed in proximal and distal sciatic nerve trunks at clamping wounds in sequence to stimulate the nerves, and compound muscle action potentials (CMAPs) were recorded. Amplitude and latency of the CMAPs were measured. In the same way, amplitude and latency of CMAPs at a normal side were recorded. The amplitude of the CMAPs was proportional to nerve fibers that innervate target muscle.

Figure 4:
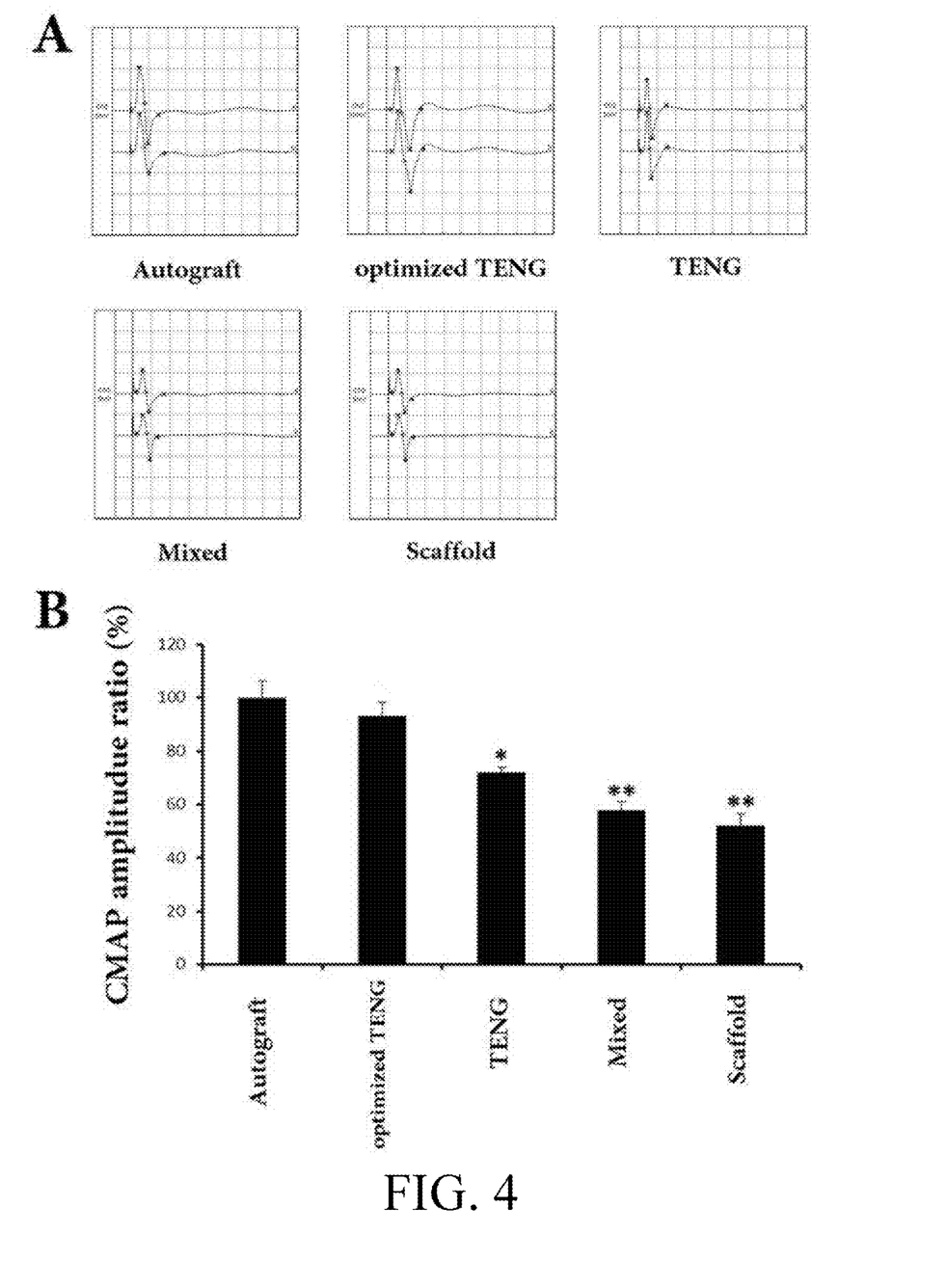
FIG. 4 shows recovery of motor function in an electrophysiological test of each experimental group 12 weeks after surgery in a sciatic nerve defect model according to Embodiment 4 of the present invention.

Results of an electrophysiological test of the compound muscle action potential are shown in FIG. 4. FIG. 4A is a representative diagram of compound muscle action potential (CMAP) of rat gastrocnemius muscle as recorded in each group 12 weeks after repair surgery of 10 mm defects of rat sciatic nerves. FIG. 4B is a histogram of amplitude of the compound muscle action potential in each group as a percentage of a positive control autologous nerve group (Autograft). The results show that the optimized motor-specific and sensory-specific tissue-engineered nerve group (optimized TENG) was not significantly different from the positive control autologous nerve group (Autograft), was significantly superior to the material only group (Scaffold) and the mixed motor and sensory group (Mixed) with P<0.01, and was also significantly superior to the motor-specific and sensory-specific tissue-engineered nerve group (TENG).

The results suggest that, under normal physiological conditions, motor nerve fibers recover significantly faster than sensory nerve fibers, so that it is clinically common that motor function is recovered and improved, and recovery of sensory function is delayed. In the optimized motor-specific and sensory-specific tissue-engineered nerve group (optimized TENG), an effect is confirmed to be optimal when a ratio of the supporting cells in the sensory-like nerve cells and the motor-like nerve cells is 3:1 through increasing a ratio of the Schwann cells and fibroblasts as the supporting cells in the sensory nerve fibers.

3. Evaluation of Recovery of Postoperative Sensory Function

A pain behavioral test was performed at 12 weeks after surgery: all animal behavioral experiments were performed in a "double-blind" experimental design scheme.

(1) A 50% paw withdrawal threshold was calculated in mechanical allodynia experiments by an Electric Von Frey dolorimeter (Stoelting company, USA) according to an up-down method. A transparent plexiglass box was placed on a metal screen. After mice were acclimated to the plexiglass box for 30 min, and then vonFrey filaments were used to vertically stimulate middle parts of hindlimb planta of the mice for 1-2 s. Paw lifting or licking behavior of the mice was regarded as a positive reaction, and otherwise, a negative reaction.

Figure 5:
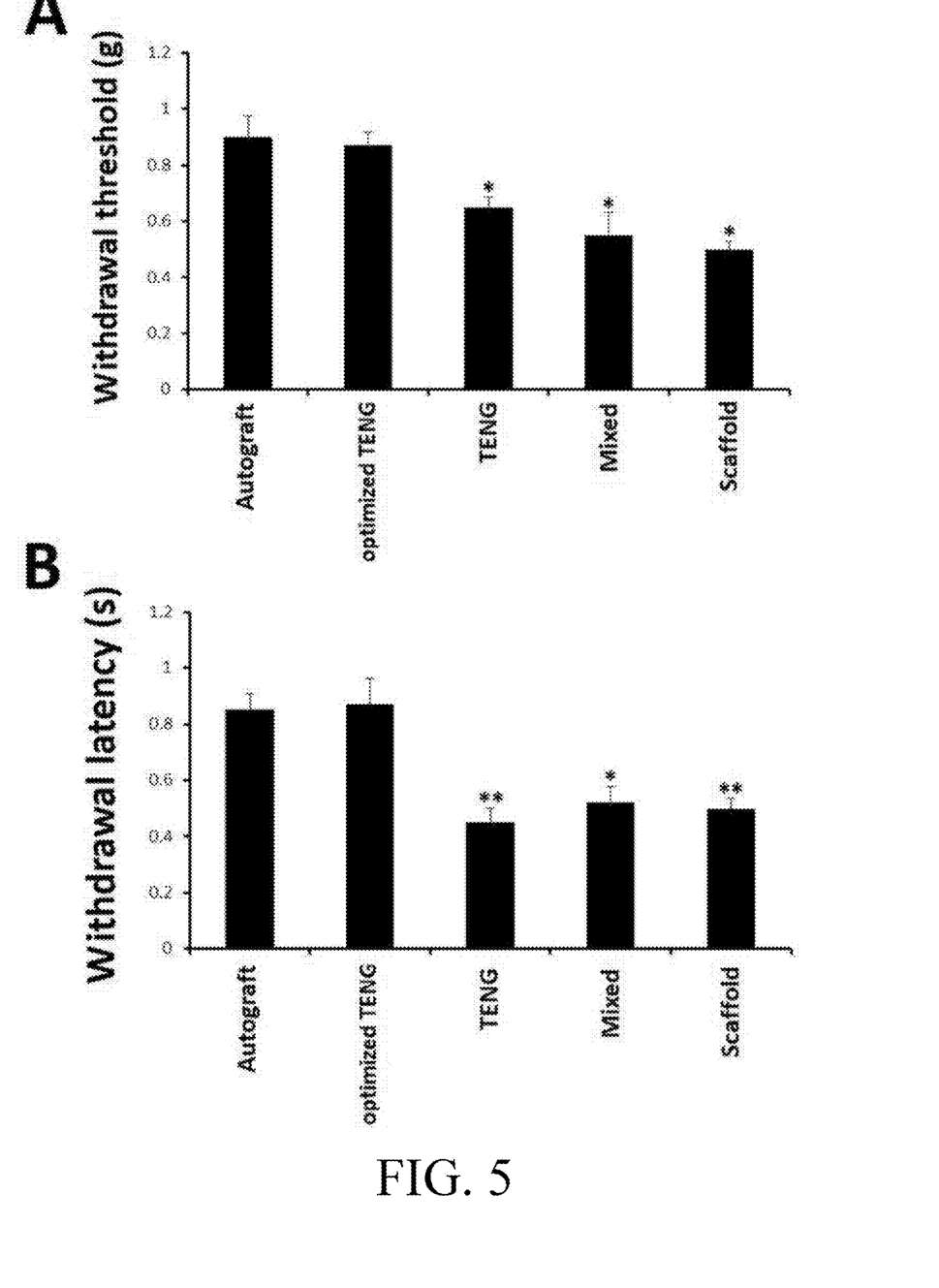
FIG. 5 shows recovery of sensory function in a pain test of each experimental group 12 weeks after surgery in a sciatic nerve defect model according to Embodiment 4 of the present invention.

Results of mechanical pain tests are shown in FIG. 5A. The results show that at 12 weeks after surgery, the mechanical pain test result for the autologous nerve group (Autograft) had recovered to near a base line (a normal value was set at 1.0), and the optimized motor-specific and sensory-specific tissue-engineered nerve group (optimized TENG) was not significantly different from the positive control autologous nerve group (Autograft), and was significantly superior to the material only group (Scaffold), the mixed motor and sensory group (Mixed), and the motor-specific and sensory-specific tissue-engineered nerve group (TENG). The results suggest that recovery of mechanical pain for the optimized motor-specific and sensory-specific tissue-engineered nerve group (optimized TENG) is significantly superior to the motor-specific and sensory-specific tissue-engineered nerve group (TENG), confirming that the effect is optimal when the ratio of the supporting cells in the sensory-like nerve cells and the motor-like nerve cells is 3:1.

(2) In thermal hyperalgesia experiments, mice were acclimated in an opaque plexiglas box (13 cm×14 cm×9 cm) with a 3 mm thick glass plate in the bottom for 30 min and were stimulated with thermal radiation to irradiate a plantar area of the mice close to the glass plate according to a Hargreaves method after combing and inquiry activities of the mice had substantially disappeared. Time from start of irradiation to the appearance of paw lifting in the mice was recorded with a cut-off time of 20 s. A mean value was calculated as paw withdrawal latency.

Results of a heat-sensitive pain test are shown in FIG. 5B. The results show that at 12 weeks after surgery, the value of the heat-sensitive pain test result for the autologous nerve group (Autograft) was 0.85, which had recovered to near a base line (the normal value was set at 1.0), while the value of the optimized motor-specific and sensory-specific tissue-engineered nerve group (optimized TENG) was 0.87, which was not significantly different from the positive control autologous nerve group (Autograft), and was significantly superior to the material only group (Scaffold), the mixed motor and sensory group (Mixed), and the motor-specific and sensory-specific tissue-engineered nerve group (TENG). The results suggest that recovery of heat-sensitive pain for the optimized motor-specific and sensory-specific tissue-engineered nerve group (optimized TENG) is significantly superior to the motor-specific and sensory-specific tissue-engineered nerve group (TENG), further confirming that the effect is optimal when the ratio of the supporting cells in the sensory-like nerve cells and the motor-like nerve cells is 3:1.

What is claimed is:

1. A differential tissue-engineered nerve, wherein it comprises motor-like nerves and sensory-like nerves, the motor-like nerve comprises a motor-like nerve outer tube and a motor-like nerve fiber in the outer tube, Schwann cells and/or fibroblasts derived from motor nerves are contained in surface or pores of the motor-like nerve outer tube and a transsynaptic signal molecule Neuroligin-1 is contained in surface or pores of the motor-like nerve fiber; and the sensory-like nerve comprises a sensory-like nerve outer tube and a sensory-like nerve fiber in the outer tube, Schwann cells and/or fibroblasts derived from sensory nerves are contained in surface or pores of the sensory-like nerve outer tube and a transsynaptic signal molecule Neuroligin-2 is contained in surface or pores of the sensory-like nerve fiber.

2. The differential tissue-engineered nerve according to claim 1, wherein a ratio of the number of the Schwann cells and/or fibroblasts derived from the motor nerves to the number of the Schwann cells and/or fibroblasts derived from the sensory nerves is 1:(1 to 5).

3. The differential tissue-engineered nerve according to claim 2, wherein the ratio of the number of the Schwann cells and/or fibroblasts derived from the motor nerves to the number of the Schwann cells and/or fibroblasts derived from the sensory nerves is 1:3.

4. The differential tissue-engineered nerve according to claim 1, wherein a mass ratio of Neuroligin-1 to Neuroligin-2 is 1:1.

5. The differential tissue-engineered nerve according to claim 1, wherein a transsynaptic signal molecule Neurexin-1β is also contained in the surface or pores of the motor-like nerve fibers and/or sensory-like nerve fibers.

6. The differential tissue-engineered nerve according to claim 5, wherein a mass ratio of Neurogligin-1 to Neurexin-1β on the motor-like nerve fibers is 1:(0.01-10), and a mass ratio of Neuroligin-2 to Neurexin-1β on the sensory-like nerve fibers is 1:(0.01-10).

7. The differential tissue-engineered nerve according to claim 6, wherein the mass ratio of Neurogligin-1 to Neurexin-1β on the motor-like nerve fibers is 1:5, and the mass ratio of Neuroligin-2 to Neurexin-1β on the sensory-like nerve fibers is 1:5.

8. The differential tissue-engineered nerve according to claim 5, wherein the transsynaptic signal molecules Neuroligin-1, Neuroligin-2 and Neurexin-1β are embedded in microspheres.

9. The differential tissue-engineered nerve according to claim 1, wherein the motor-like nerves and the sensory-like nerves are arranged in a multi-branched manner in one or more of a parallel type, a Y type, a dendritic type, and a tooth comb type.

\* \* \* \* \*